United States Patent [19]

Akimoto et al.

[11] Patent Number: 4,916,066
[45] Date of Patent: Apr. 10, 1990

[54] PROCESS FOR PRODUCTION OF BISHOMO-GAMMA-LINOLENIC ACID

[75] Inventors: Kengo Akimoto, Osaka; Yoshifumi Shinmen, Kyoto; Hideaki Yamada, Kyoto; Sakayu Shimizu, Kyoto, all of Japan

[73] Assignee: Suntory Limited, Osaka, Japan

[21] Appl. No.: 286,856

[22] Filed: Dec. 20, 1988

[30] Foreign Application Priority Data

Dec. 21, 1987 [JP] Japan ................................ 62-321551
Mar. 9, 1988 [JP] Japan ................................ 63-53642

[51] Int. Cl.$^4$ ..................... C12P 7/64; C12R 1/645; C12R 1/66; C12R 1/785
[52] U.S. Cl. ................................... 435/134; 435/136; 435/911; 435/913; 435/929; 435/931
[58] Field of Search ............... 435/136, 134, 911, 913, 435/925

[56] References Cited

FOREIGN PATENT DOCUMENTS 0252716 1/1988 European Pat. Off. .

OTHER PUBLICATIONS

CA08-148917(17) Shinmen et al EP-252716, Jan. 13, 1988.
Biotech 86-12760 (J61177990) Aug. 9, 1986.
Biotech 88-10352 (EP276982) Mar. 3, 1988.
Biotech 88-04030 (EP252716) Jan. 13-1988.
Biotech 88-06100 (J63044891) Feb. 25, 1988.
Biotech 88-02021 Yamada et al. Fat. Sci. Tech (1987) 89, 12, 469.
Derwent ABS 77-48096Y/27 (J52064484) 5-1977 Lizuka.
Derwent ABS 88-149118/22 (EP269351) 6-88 Nishimura et al.
"List of Cultures", Institute for Fermentation Osaka, Eighth Edition, vol. 1 (1988) pp. 166-167.
"List of Cultures", Institute for Fermentation Osaka, Sixth Edition (1978) pp. i, 8, 29, 30, 51, 73, 74, 88, 160.
"List of Cultures", Central Bureau Voor Schimmel cultures, Baarn, The Netherlands (1987) pp. iii-15, 86, 87, 122, 274.

*Primary Examiner*—Herbert J. Lilling
*Attorney, Agent, or Firm*—Burns, Doane, Swecker & Mathis

[57] ABSTRACT

A process for the production of bishomo-γ-linolenic acid characterized by adding an additive to a culture medium, which additive is preferably selected from sesame oil, peanut oil, an extract from sesame oil or sesame seeds, and a lignan compound present in the extract from sesame oil or sesame seeds. The process uses, as a producer microorganism, a microorganism capable of producing arachidonic acid.

10 Claims, 3 Drawing Sheets

PROCESS FOR PRODUCTION OF BISHOMO-GAMMA-LINOLENIC ACID

BACKGROUND OF THE INVENTION

1. Field of The Invention

The present invention relates to a process for the production of bishomo-γ-linolenic acid and a lipid containing bishomo-γ-linolenic acid.

2. Description of the Related Art

It is known that bishomo-γ-linolenic acid (cis-8,11,14-eicasatrienoic acid) is present in fish oils and and seaweed as a fatty acid component thereof, but since the content thereof is very low, purified bishomo-γ-linolenic acid produced therefrom is very expensive, and therefore, an efficient process for the production thereof is urgently required. To this end, various processes for the production of bishomo-γ-linolenic acid using microorganisms have been proposed, but none of those processes is satisfactory.

SUMMARY OF THE INVENTION

Accordingly, the present invention provides a process whereby bishomo-γ-linolenic acid can be efficiently produced by using an inexpensive culture medium.

The present inventors found that, when a microorganism capable of producing arachidonic acid is cultured in a medium containing sesame oil or peanut oil, the production of arachidonic acid is suppressed and the amount of bishomo-γ-linolenic acid produced is increased.

The present inventors also found that the effective ingredients in sesame oil can be extracted with an organic solvent which is substantially immiscible with the sesame oil, such as acetone, and that these ingredients comprise at least sesamin, sesaminol, episesamin, episesaminol, and sesamolin. The present inventors further found that effective ingredients can be extracted from sesame seeds with an organic solvent, and that these ingredients comprise at least 2-(3,4-methylenedioxyphenyl)-6-(3-methoxy-4-hydroxyphenyl)-3,7-dioxabicyclo [3.3.0] octane, 2,6-bis-(3-methoxy-4-hydroxyphenyl)-3,7-dioxabicyclo [3.3.0] octane, 2-(3,4-methylenedioxyphenyl)-6-(3-methoxy-4-hydroxyphenoxy)-3,7-dioxabicyclo [3.3.0] octane.

Accordingly, the present invention provides a process for the production of bishomo-γ-linolenic and, comprising the steps of:

culturing a microorganism capable of producing arachidonic acid in a culture medium containing an additive selected from the group consisting of sesame oil, peanut oil, and a mixture thereof, to produce bishomo-γ-linolenic acid or a lipid containing bishomo-γ-linolenic acid; or adding the additive to a culture medium in which the microorganism has been grown, and then further culturing the microorganism to produce bishomo-γ-linolenic acid or a lipid containing bishomo-γ-linolenic acid; and recovering the bishomo-γ-linolenic acid.

The present invention also provides a process for the production of a lipid containing bishomo-γ-linolenic acid, comprising the steps of:

culturing a microorganism capable of producing arachidonic acid in a culture medium containing an additive selected from the group consisting of sesame oil, peanut oil, and a mixture thereof, to produce a lipid containing bishomo-γ-linolenic acid; or adding the additive to a culture medium in which the microorganism has been grown, and then further culturing the microorganism to produce a lipid containing bishomo-γ-linolenic acid; and recovering the lipid containing bishomo-γ-linolenic acid.

The present invention further provides a process for the production of bishomo-γ-linolenic acid, comprising the step of:

culturing a microorganism capable of producing arachidonic acid in a culture medium containing an additive selected from the group consisting of an extract from sesame oil with a solvent which is substantially immiscible with the sesame oil and an extract from sesame seeds with a solvent which is substantially immiscible with the sesame oil to produce bishomo-γ-linolenic acid or a lipid containing bishomo-γ-linolenic acid; or adding the additive to a culture medium in which the microorganism has been grown, and then further culturing the microorganism to produce bishomo-γ-linolenic acid or a lipid containing bishomo-γ-linolenic acid; and recovering the bishomo-γ-linolenic acid.

The present invention also provides a process for the production of a lipid containing bishomo-γ-linolenic acid, comprising the steps of:

culturing a microorganism capable of producing arachidonic acid in a culture medium containing an additive selected from the group consisting of an extract extracted from sesame oil with a solvent which is immiscible with the sesame oil and an extract from sesame seeds to produce a lipid containing bishomo-γ-linolenic acid; or adding the additive to a culture medium in which the microorganism has been grown, and then further culturing the microorganism to produce a lipid containing bishomo-γ-linolenic acid; and recovering the lipid containing bishomo-γ-linolenic acid.

The present invention provides another process for the production of bishomo-γ-linolenic acid, comprising the steps of:

culturing a microorganism capable of producing arachidonic acid in a culture medium containing an additive selected from the group consisting of sesamin sesaminol, episesamin, episesaminol, sesamolin, 2-(3,4-methylenedioxyphenyl)-6-(3-methoxy-4-hydroxyphenyl)-3,7-dioxabicyclo [3.3.0] octane, 2,6-bis-(3-methoxy-4-hydroxyphenyl)-3,7-dioxabicyclo [3.3.0]octane, 2-(3,4-methylenedioxyphenyl)-6-(3-methoxy-4-hydroxyphenoxy)-3,7-dioxabicyclo [3.3.0]octane, and a mixture thereof, to produce bishomo-γ-linolenic acid or a lipid containing bishomo-γ-linolenic acid; or adding the additive to a culture medium in which the microorganism has been grown, and then further culturing the microorganism to produce bishomo-γ-linolenic acid or a lipid containing bishomo-γ-linolenic acid; and recovering the bishomo-γ-linolenic acid.

The present invention still further provides a process for the production of a lipid containing bishomo-γ-linolenic acid, comprising the steps of:

culturing a microorganism capable of producing arachidonic acid in a culture medium containing an additive selected from the group consisting of sesamin, sesaminol, episesamin, episesaminol sesamolin, 2-(3,4-methylenedioxyphenyl-6-(3-methoxy-4-hydroxyphenyl)-3,7-dioxabicyclo [3.3.0] octane, 2,6-bis-(3-methoxy-4-hydroxyphenyl)-3,7-dioxabicyclo [3.3.0] octane, 2-(3,4-methylene dioxyphenyl)-6-(3-methoxy-4-hydroxyphenoxy)-3,7-dioxabicyclo [3.3.0] octane, and a mixture thereof, to produce a lipid containing bishomo- γ-linolenic acid; or adding the additive to a culture medium in which the microorganism has been grown, and then culturing the microorganism to produce a lipid containing bishomo-γ-linolenic acid; and recovering the lipid containing bishomo-γ-linolenic acid.

Moreover, the present invention provides a process for the production of bishomo-γ-linolenic acid, comprising the steps of:

culturing a microorganism capable of producing arachidonic acid in a culture medium containing an additive selected from the group consisting of Tarragon extract, Dill Seed extract, Parsley extract, Turmeric extract, Nutmeg extract, and a mixture thereof, to produce bishomo-γ-linolenic acid or a lipid containing bishomo-γ-linolenic acid; or adding the additive to a culture medium in which the microorganism has been grown, and then further culturing the microorganism to produce bishomo-γ-linolenic acid or a lipid containing bishomo-γ-linolenic acid; and recovering the bishomo-γ-linolenic acid.

The present invention also provides a process for the production of a lipid containing bishomo-γ-linolenic acid, comprising the steps of:

culturing a microorganism capable of producing arachidonic acid in a culture medium containing an additive selected from the group consisting of Tarragon extract, Dill Seed extract, Parsley extract, Turmeric extract, Nutmeg extract, and a mixture thereof, to produce a lipid containing bishomo-γ-linolenic acid; or adding the additive to a culture medium in which the microorganism has been grown, and then further culturing the microorganism to produce a lipid containing bishomo-γ-linolenic acid; and recovering the lipid containing bishomo-γ-linolenic acid.

DESCRIPTION OF THE PREFERRED EMBODIMENTS

Figure 1:
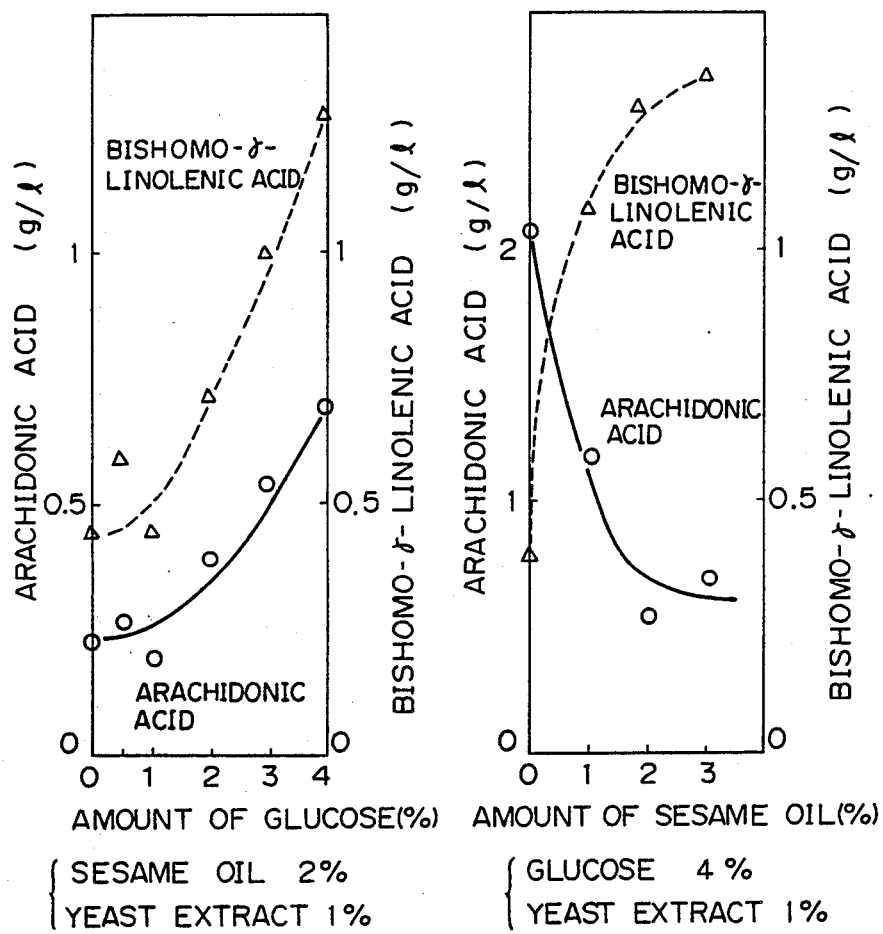
FIG. 1 represents graphs showing the relationship between the amounts of arachidonic acid and bishomo-γ-linolenic acid, and the concentration of glucose or sesame oil added to a culture medium.

According to the present invention, any microorganism capable of producing arachidonic acid can be used as the producer microorganisms. These microorganisms include those belonging to the genera *Mortierella, Conidiobolus, Pythium. Phytophthora, Penicillium, Cladosporium, Mucor, Fusarium, Aspergillus, Rhodotorula,* and *Entomophthora.* Microorganisms belonging to the genus *Mortierella* include, for example, *Mortierella elongata* IFO 8570, *Mortierella exigua* IFO 8571, *Mortierella hygrophila* IFO 5941, *Mortierella alpina* IFO 8568 and *Mortierella parvispora* IFO 8574. Other strains which can be used in the present invention include *Conidiobolus heterosporus* CBS 138.57, *Pythium irregulare* CBS 494 86, *Conidiobolus thromoboides* CBS 183.60, *Penicillium cyaneum* IFO 5337, *Cladosporium claudosforiodes* IFO 30314, *Mucor ambiguus* IFO 6742, *Aspergillus candidus* IFO 8816, *Rhodotorula glutinis* IFO 0695, *Fusarium oxysporum* IFO 5942, *Cladosporium sphaerospermum* IFO 6377, and *Entomophthora ignobilis* CBS 181.60.

The above-mentioned strains having an IFO number are stored in the Osaka Institute for Fermentation; 17–85, Joso-honmachi 2-chome, Yodogawa-ku, Osaka 532, Japan, and are available to the public without limitation. The above-mentioned strains having a CBS number are stored in the Central Bureau Voor Schimmelcultures, Boorn, Netherlands, and are available to the public without limitation.

Moreover, a strain *Mortierella elongata* SAM 0219, can be used. This strain was newly isolated from soil and identified by the present inventors, and was deposited with the Fermentation Research Institute, Agency of Industrial Science and Technology (FRI), Higashi 1-1-3, Tsukuba-shi, Ibaraki-ken, Japan as FERM P-8703 on Mar. 19, 1986, and transferred to International Deposition under the Budapest Treaty as FERM BP-1239 on Dec. 22, 1986.

Spores, mycelia, or a preculture are used as an inoculum for culturing the present strains. The medium used may be a liquid or solid medium. A liquid medium contains as a carbon source, for example, glucose, fructose, xylose, saccharose, maltose, soluble starch, molasses, glycerol, or mannitol. Nitrogen sources include organic substances such as peptones, yeast extract, meat extract, casamino acid, corn steep liquor, urea and inorganic substances such as sodium nitrate, ammonium nitrate, ammonium sulfate, and the like. If necessary, inorganic salts such as phosphate salts, magnesium sulfate, ferrous sulfate and cupric sulfate, and vitamins may be included in a medium. The concentration of these components is selected so that such components do not adversely affect the growth of the microorganism used. Practically, the concentration of the carbon source is 0.1 to 30% by weight, preferably 1 to 10% by weight, relative to the total weight of the medium. The concentration of the nitrogen source is 0.01 to 5% by weight, preferably 0.1 to 2% by weight, relative to the total weight of the medium.

The culturing temperature is from 5° C. to 40° C., and the pH value of the medium is 4 to 10, preferably 6 to 9. Culturing is preferably carried out with aeration and-/or agitation, while shaking in a liquid medium, or while standing, and is usually carried out for 2 to 10 days.

When culturing is carried out in a solid medium, the solid medium is composed of wheat bran, chaff or rice bran supplemented with water in an amount of 50 to 100% by weight relative to the wheat bran, chaff or rice bran. If necessary, the medium is supplemented with a small amount of nitrogen source, inorganic salts, and or minor nutrients. Culturing is carried out at a temperature of 5° C. to 40° C., preferably 20°·C. to 30° C., for 3 to 14 days.

According to the present invention, a microorganism capable of producing arachidonic acid is cultured in a medium containing an additive, to produce bishomo-γ-linolenic acid. The additives include sesame oil, peanut oil, and a mixture of these oils. These oils can be in a crude form of a purified form.

Moreover, the additive can be an extract from sesame oil. To obtain the extract, sesame oil is extracted with an organic solvent which is substantially immiscible with the sesame oil and can extract and dissolve effective ingredients. The organic solvents are, for example, acetone, methyl ethyl ketone, diethyl ketone, methanol, ethanol, and the like. To extract the effective ingredients, for example, sesame oil and the solvent are homogenously mixed, and the mixture is allowed to stand at a low temperature. Phases are separated by a conventional procedure such as centrfugation to obtain an organic phase, which is then evaporated to obtain an extract. Alternatively, an extract useful for the present invention can be obtained from sesame seeds. In this case, sesame seeds, if necessary after grinding, are extracted with any solvent able to extract the sesame oil, for example, an organic solvent described above. After separating the solvent from the residue, the solvent is evaporated to obtain an extract. An extract obtained from sesame oil or sesame seeds contains lignans such as sesamin, sesaminol, episesamin, episesaminol, sesamolin, 2-(3,4-methylenedioxyphenyl)-6-(3-methoxy-4-hydroxyphenyl)-3,7-dioxabicyclo [3.3.0] octane, 2,6-bis-(3-methoxy-4-hydroxyphenyl)-3,7-dioxabicyclo [3.3.0] octane, 2-(3,4-methylenedioxyphenyl)-6-(3-methoxy-4-hydroxyphenoxy)-3,7-dioxabicyclo [3.3.0] octane. Therefore, in accordance with the present invention, the abovementioned compound alone, or any combination of at least two of the above-mentioned compounds, can be used as the additive. All of the above-mentioned compounds are known and are commercially available. Alternatively, there compounds can be isolated from the above-mentioned extract from sesame oil or sesame seeds. To this end, the extract can be separated by a conventional procedure, such as column chromatography, high performance liquid chromatography, distillation, crystallization, or a combination thereof.

Moreover, the additives used in the present invention include extracts from various kinds of plants, for example, spicy plants such as Tarragon, Dill Seed, Parsley, Turmeric, Nutmeg, and the like. Moreover, extracts can be prepared from spicery made from these plants. There extracts can be prepared by extracting the above-mentioned materials with a conventional solvent such as dichloromethane, ethanol, methanol, ethyl ether or the like.

The amount of the additive to be added to a culture medium is approximately as follows. Sesame oil, peanut oil, or a total amount of a mixture thereof, at 0.001 to 10% by weight, preferably 0.5 to 10% by weight relative to the amount of the medium. The extract from sesame oil or sesame seeds is used in an amount of $3 \times 10^{-3}$ to $3 \times 10^{-1}\%$ by weight relative to the amount of the medium. The above-mentioned lignan compounds are used in an amount of $1 \times 10^{-3}$ to $1 \times 10^{-1}\%$ by weight relative to the amount of the medium. Where a mixture of two or more lignans is used, this amount is intended to be a total amount of the mixture.

The above-mentioned additive can be added to a culture medium before inoculation, or immediately after inoculation and before the onset of culturing. Alternatively, the additive can be added to a medium during culturing, or both before the onset of culturing and during culturing. When such an additive is used during culturing, it is added at one time, stepwise, or continuously.

Note, to enhance the effect of the additive olive oil, soybean oil, cottonseed oil, coconut oil, or the like, which would increase the production of arachidonic acid, can be added to the culture medium.

During the culturing, a lipid containing a large amount of bishomo-γ-linolenic acid is intracellularly accumulated. Where culturing is carried out in a liquid medium, bishomo-γ-linolenic acid is recovered, for example, as follows After the culturing cells are collected from the culture broth by a conventional means such as filtration or centrifugation, the cells are washed with water, and preferably, the washed cells are dried.

Drying is carried out by, for example, lyophilization or air-drying. The dried product is treated with an organic solvent or a mixture thereof, preferably under a nitrogen stream, to extract a lipid containing bishomo-γ-linolenic acid. The organic solvent or mixture thereof is, for example, ethers such as ethyl ether, hydrocarbons such as hexane, alcohols such as methanol or ethanol halo-hydrocarbons such as chloroform or dichloromethane, petroleum ether, as well as a mixture of chloroform, methanol and water, or a combination of methanol and petroleum ether alternately used. By distilling off the solvent, a lipid containing bishomo-γ-linolenic acid is obtained.

Alternatively wet cells or the culture broth can be subjected to direct extraction. In such a case, a water-miscible solvent such as methanol or ethanol, or a water-miscible solvent mixture comprising the water-miscible solvent and water or other organic solvent is used. The extraction procedure is the same as described for dried cells.

The lipid thus obtained contains bishomo-γ-linolenic acid in the form of a lipid compound such as fat. Although bishomo-γ-linolenic acid can be isolated in the form of free bishomo-γ-linolenic acid, it is preferably isolated in the form of an ester with a lower alcohol, for example, as methyl ester. By converting bishomo-γ-linolenic acid to such an ester, it is easily separated from other lipid components, and from other undesirable fatty acids formed during culturing, such as palmitic acid, oleic acid, linoleic acid and the like, which are also esterified at the same time as bishomo-γ-linolenic acid is esterified. To obtain methyl ester of bishomo-γ-linolenic acid, for example, the lipid prepared as described above is treated with a 5 to 10% hydrochloric acid solution in absolute methanol or a 10 to 50% $BF_3$ solution in methanol for 1 to 24 hours at a room temperature.

The mixture thus obtained is extracted with an organic solvent such as hexane, ethyl ether or ethyl acetate, to recover methyl ester of bishomo-γ-linolenic acid. Next, the extract is dried over anhydrous sodium sulfate, and the solvent is distilled under a reduced pressure to obtain a residue mainly comprising a fatty acid mixture. The mixture contains, in addition to methyl ester of bishomo-γ-linolenic acid, methyl plamitate, methyl stearate, methyl oleate and the like. From the mixture, methyl ester of bishomo-γ-linolenic acid is isolated by column chromatography, low temperature crystalization, a urea adducting method, or a combination thereof.

The isolated methyl ester of bishomo-γ-linolenic acid is then hydrolyzed with an alkali and extracted with an organic solvent such as ethyl ether, ethyl acetate, or the like to obtain bishomo-γ-linolenic acid in a free form.

Alternatively, bishomo-γ-linolenic acid can be obtained, without conversion to methyl ester, by alkalolysis with, for example, 5% sodium hydroxide at a room temperature for 2 to 3 hours, followed by extraction of the fatty acids from the alkalolysis product and isolation of bishomo-γ-linolenic acid.

EXAMPLES

The present invention will now be further illustrated by, but is by no means limited to, the following examples.

EXAMPLE 1

Two ml each of a culture medium A containing 2.5% glucose and 1% yeast extract (pH 6.0) and a culture medium B containing 0.5% glucose, 2% sesame oil, and 1% yeast extract (pH 6.0) were put into test tubes having a screw cap, and the whole was autoclaved at 120° C. for 20 minutes. *Mortierella isabellina* IFO 7884, *Mortierella vinacea* IFO 7875, *Mortierella humicola* IFO 8289, *Mortierella nana* IFO 8796, *Mortierella alpina* IFO 8568, *Mortierella elongata* IFO 8570, and *Mortierella parvispora* IFO 8574 were separately inoculated to each of the above-mentioned two media, and cultured on a reciprocating shaker at 110 rpm, for six days at 28° C. After the culturing, each culture broth was evaporated to dryness in a centrifugal evaporator at 60° C. for two hours. To the residue were added 2 ml of methylene chloride and 2 ml of 10% hydrochloric acid in absolute methanol, and the whole was incubated at 50° C. for three hours to esterify produced fatty acids. To the mixture were added 4 ml of n-hexane and 1 ml of water to extract the fatty acids methyl esters. The extraction was carried out twice, and the extractants were combined and evaporated in a centrifugal evaporator at 40° C. for one hour to eliminate the solvent. The fatty acid methyl esters thus obtained were analyzed by gas chromatography, and the results are shown in Table 1.

TABLE 1

| Producer strains | Fatty acids produced | | |
|---|---|---|---|
| | γ-linolenic acid (mg/l) | bishomo-γ-linolenic acid (mg/l) | arachinonic acid (mg/l) |
| M. isabellina | 101.6 | | |
| | 143.4 | | |
| M. vinacea | 122.4 | | |
| | 195.4 | | |
| M. humicola | 122.5 | | |
| | 215.7 | | |
| M. nana | 195.6 | | |
| | 216.8 | | |
| M. alpina | 113.0 | 70.7 | 617.0 |
| | 276.1 | 301.5 | 141.7 |
| M. elongata | 72.9 | 67.2 | 430.3 |
| | 160.7 | 125.0 | 92.5 |
| M. parvispora | 116.7 | 81.9 | 268.2 |
| | 361.9 | 398.1 | 55.8 |

Upper figures: results from the medium A
Lower figures: results from the medium B As seen from Table 1, when a microorganism capable of producing arachidonic acid was cultured in a medium containing sesame oil, the promotion of arachiodonic acid was suppressed, and a large amount of bishomo-γ-linolenic acid was produced. Note, the produced bishomo-γ-linolenic acid was identified by Mass spectrum and NMR analysis.

EXAMPLE 2

Four ml each of a medium containing 4% glucose, 1% yeast extract, and 2% sesame oil (pH 6.0) (medium A), a medium containing 4% glucose, 1% yeast extract and 2% peanut oil (pH 6.0) (medium B), a medium containing 4% glucose, 1% yeast extract, and 2% olive oil (pH 6.0) (medium C), and a medium containing 4% glucose and 1% yeast extract (pH 6.0) (medium D) were put into 20 ml Erlenmeyer flasks and autoclaved at 120° C. for 20 minutes, 200 ml of a spore suspension of *Mortierella alpina* IFO 8568 was added to each medium, and culturing was carried out on a reciprocating shaker at 110 rpm, for 8 days at 20° C. After the culturing, each culture broth was filtrated to recover cultured cells, which were then thoroughly washed with water. The washed cells were dried in a centrifugal evaporation, and the dried cells were subjected to hydrolysis, methyl-esterification, and extraction as described in Example 1, and fatty acid methyl esters thus obtained were analyzed by gas chromatography. The results are shown in Table 2.

TABLE 2

| | Product | | |
|---|---|---|---|
| Additive | Dry cell (g/l) | bishomo-γ-linolenic acid (g/l) | Arachidonic acid (g/l) |
| none | 17.9 | 0.43 | 3.48 |
| Peanut oil 2% | 35.8 | 0.99 | 2.26 |
| Sesame oil 2% | 35.3 | 1.53 | 0.92 |
| Olive oil 2% | 35.9 | 0.51 | 3.58 |

As seen from Table 2, the addition of sesame oil or peanut oil to a culture medium suppressed the production of arachidonic acid and stimulated the production of bishomo-γ-linolenic acid. Note, olive oil representing an oil other than sesame oil and peanut oil did not stimulate the production of bishomo-γ-linolenic acid.

EXAMPLE 3

Ten ml each of a medium containing 0, 0.5, 1, 2, 3, or 4% glucose, 1% yeast extract, and 2% sesame oil (pH 6.0), and a medium containing 4% glucose, 1% yeast extract, and 0, 1, 2, or 3% sesame oil (pH 6.0) was put into 50 ml Erlenmeyer flasks and autoclaved at 120° C. for 20 minutes, 250 μl of a spore suspension of *Mortierella alpina* IFO 8568 was inoculated to the medium, and culturing was carried out on a reciprocating shaker at 110 rpm, for seven days at 28° C. After culturing, the filtration of the cultured broth, washing cells with water, drying of cells, hydrolysis of the lipid, methyl-esterification of the fatty acids, and extraction of the methyl esters were carried out by the same procedures as described in Example 1. The fatty acid methyl esters thus obtained were analyzed by gas chromatography, and the results are shown in FIG. 1.

As seen from FIG. 1, the production of arachidonic acid and bishomo-γ-linolenic acid was increased in accordance with the increase of glucose added, and the addition of sesame oil suppresses the production of arachidonic acid and stimulates the production of bishomo-γ-linolenic acid.

EXAMPLE 4

100 ml each of a medium containing 5% glucose, 1% yeast extract and 2% sesame oil (pH 6.0) was put into a 500 ml Erlenmeyer flask and autoclaved at 120° C. for 20 minutes, 2.5 ml of a spore suspension of *Mortierella alpina* IFO 8568 was inoculated to the medium, and culturing was carried out on a reciprocating shaker at 110 rpm, for seven days at 20° C. Filtration of the cultured broth, washing the cells with water, drying the cells, hydrolysis of a lipid, methyl-esterification of the fatty acids, and extraction of the methyl esters were carried out by the same procedures as described in Example 1, to obtain 12.0 g of a mixture of fatty acid methyl esters. This mixture contained methyl bishomo- γ-linolenate in an amount of 9.3% by weight relative to a total amount of the mixture, which corresponds to 2.23 g/l of the medium, and 55.8 mg/g of dry cells. The mixture contained methyl arachidonate in an amount of 6.6% by weight relative to a total amount of the mixture, which corresponds to 1.58 g/l of the medium, and 39.4 mg/g of dry cells.

EXAMPLE 5

2 ml each of a medium containing 4% glucose, 1% yeast extract, and 1% sesame oil (pH 6.0), and a medium containing 4% glucose and 1% yeast extract (pH 6.0) was put into a 10 ml Erlenmeyer flask, and autoclaved at 120° C. for 20 minutes. *Conidiobolus heterosporus* CBS 38.57, *Pythium irregulare* CBS 494.86, *Phytophthora infestans* IFO 4872, *Conidiobolus thromoboides* CBS 183.60, *Penicillium cyaneum* IFO 5337, *Cladosporium claudosporiodes* IFO 30314, *Mucor ambiguus* IFO 6742, *Aspergillus candidus* IFO 8816, *Rhodotorula glutinis* IFO 0695, *Fusarium oxysporum* IFO 5942, *Cladosporium sphaerospermum* IFO 6377, or *Entomophthora ignobilis* CBS 181.60 were separately inoculated to the above-mentioned media, and cultured on a reciprocating shaker at 110 rpm, for seven days at 28° C. Filtration of the cultured broth, washing the cells with water, drying the cells, hydrolysis of the fatty acids, methyl-esterification of the fatty acids, and extraction of the methyl esters are carried out by the same procedures as described in Example 1 to obtain a mixture of the fatty acid methyl esters. The mixture was analyzed by gas chromatography, and the results are shown in Table 3.

TABLE 3

Amount of production of bishomo-γ-linolenic acid per medium (mg/l)

| Producer strain | Sesame oil Absent | Sesame oil Present |
|---|---|---|
| *Conidiobolus heterosporus* CBS 138.57 | 40.7 | 520.1 |
| *Pythium irregulare* CBS 494.86 | 12.3 | 56.3 |
| *Phytophthora infestans* IFO 4872 | 10.2 | 93.4 |
| *Conidiobolus thromoboides* CBS 183.60 | 14.1 | 77.1 |
| *Penicillium cyaneum* IFO 5337 | 7.8 | 19.3 |
| *Cladosporium claudosporiodes* IFO 30314 | 3.0 | 12.3 |
| *Mucor ambiguus* IFO 6742 | 3.6 | 11.4 |
| *Aspergillus candidas* IFO 8816 | 7.4 | 22.1 |
| *Phodotorula glutinis* IFO 0695 | 4.3 | 17.3 |
| *Fusarium oxysporum* IFO 5942 | 4.4 | 21.4 |
| *Cladosporium sphaerospermum* IFO 6377 | 5.1 | 19.4 |
| *Entomophthora ignobilis* CBS 181.60 | 8.3 | 24.1 |

EXAMPLE 6

4 ml each of a culture medium containing 4% glucose and 1% yeast extract was put into 20 ml Erlenmeyer flasks and autoclaved at 120° C. for 20 minutes, 200 μl of a spore suspension of *Mortierella alpina* IFO 8568 was inoculated to the medium, and culturing was carried out on a reciprocating shaker at 110 rpm, for two days at 28° C., and then 80 mg (2%) of sesame oil was added to the culture. Culturing was further continued for six days. After the culturing, cultured cells were recovered by filtration, thoroughly washed with water, and dried in a centrifugal evaporator at 60° C. for two hours. The hydrolysis of fatty acids, methyl-esterifications of the fatty acids, and extraction of the fatty acid methylesters were carried out by the same procedures as described in Example 1, to obtain a fatty acid methyl ester mixture. A gas chromatography analysis of the mixture showed that an amount of bishomo-γ-linolenic acid produced per medium was 1.6 g/l.

EXAMPLE 7

In 150 ml of acetone was dissolved 20 g of sesame oil, the solution was allowed to stand overnight at −80° C., and as a result, the oil fraction settled. The whole was then filtered to obtained an acetone fraction. The acetone fraction was evaporated to obtain an acetone-soluble fraction A. The settled fraction was freed from the acetone in a rotary evaporator to obtain an acetone-treated oil. The amount by volume of the fraction A was one fiftieth of the oil.

2 ml each of a medium containing 4% glucose, 1% yeast extract, and 0, 0.5, 1, 2 or 3% sesame oil (pH 6.0); a medium containing 4% glucose, 1% yeast extract, and 0, 0.5, 1, 2 or 3% the acetone-treated oil (pH 6.0); and a medium containing 4% glucose, 1% yeast extract, and 0, 0.1, 0.2 or 0.5 mg the fraction A (pH 6.0) were put into 10 ml Erlenmeyer flasks and autoclaved at 120° C. for 20 minutes, 100 μl of a spore suspension of *Mortierella alpina* IFO 8568 was inoculated to the medium, and culturing was carried out on a reciprocating shaker at 110 rpm, for eight days at 28° C. After culturing, the cultured broth was filtrated to recover cells, which were thoroughly washed with water, and then dried. To the dried cells were added 2 ml of methylene chloride and 2 ml of a mixture of 10% hydrochloric acid in absolute methanol, and the mixture was incubated at 50° C. for three hours to methyl-esterify fatty acids. To the mixture were added 4 ml of n-hexane and 1 ml of L-water, to extract the fatty acid methyl esters. The extraction was twice repeated. The obtained organic phase was evaporated in a centrifugal evaporator at 40° C. for one hour to obtain a residue comprising fatty acid methyl esters, which was then analyzed by gas chromatography. The results are shown in FIG. 2.

Figure 2:
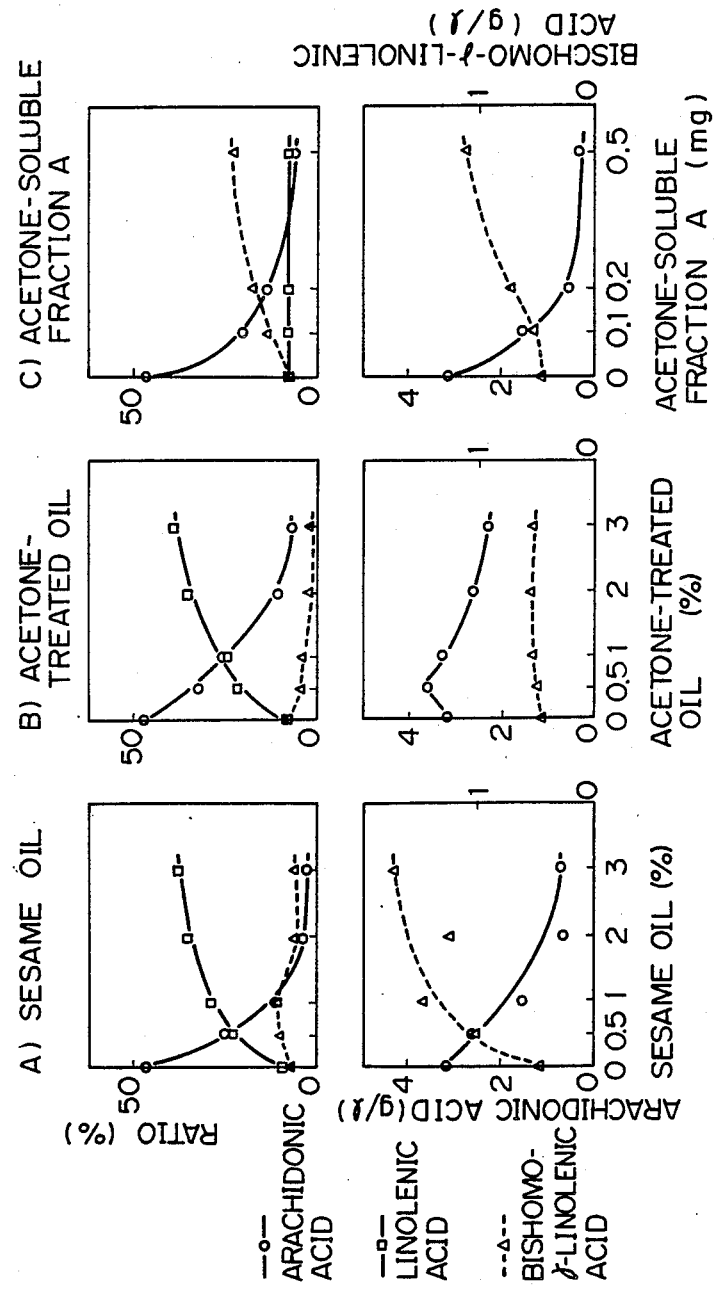
FIG. 2 represents graphs showing the relationship between the amount of sesame oil and products derived from a medium added sesame oil, acetone treated oil or acetone-soluble friction A and the amounts of various fatty acids produced.

As seen from FIG. 2, the amount of bishomo-γ-linolenic acid produced was increased by adding sesame oil per se or the acetone soluble fraction A, but was not increased by adding the acetone-treated oil. On the other hand, an amount of arachidonic acid produced was decreased by adding sesame oil or the acetone-soluble fraction A, but was not substantially affected by adding the acetone-treated oil.

This means that the effective ingredients were extracted from the sesame oil with acetone.

The ratio of the arachidonic acid produced relative to the total fatty acids produced was remarkably reduced by the addition of sesame oil, the acetone-soluble fraction A, or the acetone-treated oil. On the other hand, the ratio of linoleic acid produced relative to the total fatty acid produced was increased by the addition of sesame oil or acetone-treated oil, and was not affected by the addition of the acetone-soluble fraction A. As a result, the ratio of bishomo-γ-linolenic acid produced relative to the total of fatty acids produced was increased by the addition of the acetone-soluble fraction A.

EXAMPLE 8

The acetone-soluble fraction A obtained in Example 7 was separated by a high performance liquid chromatography using a reverse phase column (5C$_{18}$) and a mixture of methanol and water (volume ratio=60:40) as an eluent, to obtain fractions which stimulate the production of bishomo-γ-linolenic acid. One of the obtained fractions was evaporated to obtain crystal. After recrystallization, this substance was analyzed by Mass spectrometry and NMR, and confirmed to be sesamin, 2,6-bis-(3,4-methylenedioxyphenyl)-cis-3,7-dioxabicyclo [3.3.0]octane.

2 ml each of a medium containing 4% glucose, 1% yeast extract, and 0, 5, 10, 20, 35 or 50 μl of a solution of 0.4% of the sesamin preparation thus obtained in chloroform was put into a 10 ml Erlenmeyer flask, and autoclaved at 120° C. for 20 minutes, 100 μl of a spore solution of *Mortierella alpina* IFO 8568 was incubated to the medium, and culturing was carried out on a reciprocating shaker at 110 rpm, for seven days at 28° C. The filtration of the cultured broth, washing of the cells with water, drying the cells, hydrolysis of the fatty acids, methyl-esterification of the fatty acids, and extraction of the methyl esters were carried out by the same procedures an described in Example 1, to obtain a mixture of the fatty acid methyl esters. The mixture was analyzed by gas chromatography and the results are shown in FIG. 3.

Figure 3:
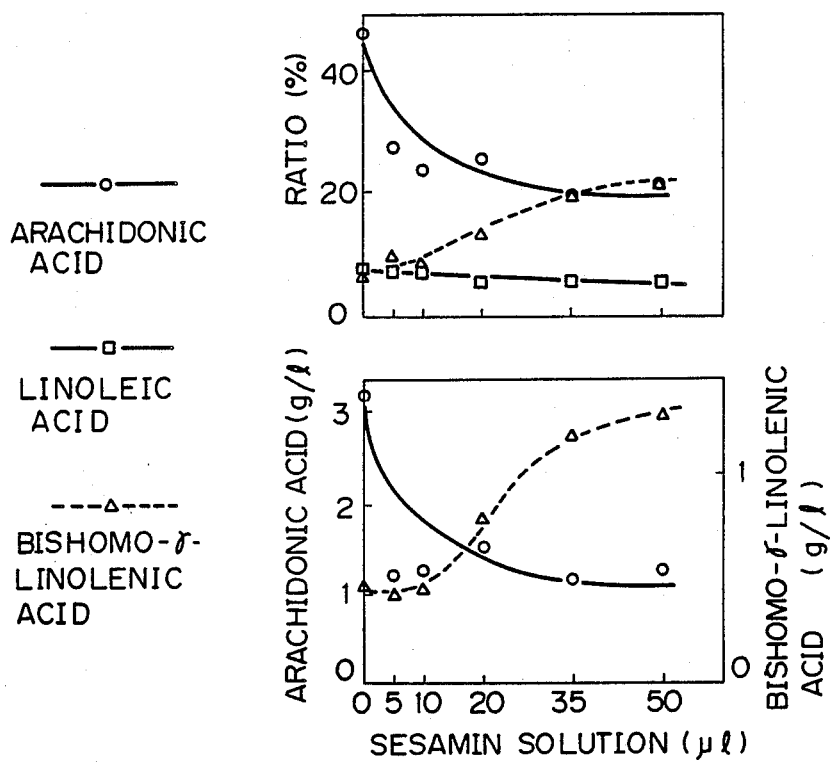
FIG. 3 represents graphs showing the relationship between an amount of sesamin added to a medium and amounts of arachidonic acid and bishomo-γ-linolenic acid produced.

As seen from FIG. 3, the amount of bishomo-γ-linolenic acid produced was increased, and the amount of arachidonic acid produced was reduced, by the addition of sesamin.

EXAMPLE 9

Two ml of a medium containing 4% glucose and 1% yeast extract was put into a 10 ml Erlenmeyer flask and autoclaved at 120° C. for 20 minutes, 100 μl of a spore suspension of *Mortierella alpina* IFO 8568 was inoculated to the medium, and culturing was carried out on a reciprocating shaker at 110 rpm, for two days at 28° C. Then 50 μl of the sesamin solution prepared in Example 8 was added to the culture, and culturing was continued for a further six days. After the culturing, the filtration of the cultured broth, washing of the cells with water, drying the cells, hydrolysis of the fatty acids, methyl-esterification of the fatty acids, and extraction of the methyl esters are carried out by the same procedures as described in Example 1, to obtain a mixture of the fatty acid methyl esters. The mixture was analyzed by gas chromatography. Bishomo-γ-linolenic acid was produced in an amount of 1.5 g/l of the cultured broth.

EXAMPLE 10

2 ml each of a medium containing 4% glucose, 1% yeast extract and 50 μl the sesamin solution prepared in Example 8 (pH 6.0), and a medium containing 4% glucose and 1% yeast extract (pH 6.0). was put into 10 ml Erlenmeyer flasks, and autoclaved at 120° C. for 20 minutes.

*Conidiobolus heterosporus* CBS 138.57, *Pythium irregulare* CBS 494.86, *Phytophthora infestans* IFO 4872, *Penicillium cyaneum* IFO 5337, *Cladosporium claudosporiodes* IFO 30314, *Mucor ambiguus* IFO 6742, *Aspergillus candidus* IFO 8816, *Rhodotorula qlutinis* IFO 0695, *Fusarium oxysporum* IFO 5942, *Entomophthora iqnobilis* CBC 181.60 were separately inoculated to the above-mentioned media, and culturing was carried out on a reciprocating shaker at 110 rpm, for seven days at 28° C. The filtration of the cultured broth, washing of the cells with water drying the cells, hydrolysis of the fatty acids, methylesterification of the fatty acid, and extraction of the methyl esters are carried out by the same procedures as described in Example 1, to obtain a mixture of the fatty acid methyl esters. The mixture was analyzed by gas chromatography and the results are shown in Table 4.

TABLE 4

| | Amount of bishomo-γ-linolenic acid per medium produced (mg/l) | |
|---|---|---|
| | Sesamin | |
| Producer strain | Absent | Present |
| *Conidiobolus heterosporus* CBS 138.57 | 38.9 | 460.3 |
| *Pythium irregulare* CBS 494.86 | 10.6 | 63.2 |
| *Phytophthora infestans* IFO 4872 | 11.7 | 72.4 |
| *Penicillium cyaneum* IFO 5337 | 7.5 | 21.1 |
| *Cladosporium claudosporiodes* IFO 30314 | 3.0 | 14.8 |
| *Mucor ambiguus* IFO 6742 | 3.2 | 10.2 |
| *Aspergillus candidas* IFO 8816 | 6.9 | 24.9 |
| *Phodotorula glutinis* IFO 0695 | 3.7 | 17.7 |
| *Fusarium oxysporum* IFO 5942 | 4.4 | 18.6 |
| *Entomophthora ignobilis* CBS 181.60 | 7.7 | 21.3 |

EXAMPLE 11

The fractions other than that containing sesamin, as prepared in Example 8, were evaporated to obtain crystals, which were then recrystallized in ethanol. The crystals, which were then analyzed by Mass spectroscopy and NMR, and confirmed to be sesaminol, i.e., 2-(3,4-methylenedioxy-6-hydroxyphenyl)-6-(3,4-methylenedioxyphenyl)-cis-3,7-dioxabicyclo [3.3.0] octane, episesaminol, and episesamin. The fractions of sasaminol, episesaminol, and episesamin were evaporated in a centrifugal evaporator, and the residues were dissolved in 200 μl of chloroform to prepare solutions of sesaminol, episesaminol, and episesamin.

2 ml each of a medium containing 4% glucose, 1% yeast extract, and 50 μl of the solution of 0.4% sesaminol, episesaminol or episesamin (pH 6.0) was put into 10 ml Erlenmeyer flasks and autoclaved at 120° C. for 20 minutes, 100 μl, of a spore suspension of *Morbierella alpina* IFO 8568 was inoculated to the medium, and culturing was carried out on a reciprocating shaker at 110 rpm, for eight days at 28° C. After culturing, the filtration of the cultured broth, washing of the cells with water, drying the cells, hydrolysis of the fatty acids, methyl-esterification of the fatty acids, and extraction of the methyl esters were carried out by the same procedures as described in Example 1, to obtain a mixture of the fatty acid methyl esters. The mixture was analyzed by gas chromatography. As a result, it was found that the amount of bishomo-γ-linolenic acid produced was greatly increased by the addition of sesaminol, episesaminol or episesamin, and the amounts of bishomo-γ-linolenic acid were 0.86, 0.71, and 0.81 g/l of the broth respectively.

EXAMPLE 12

0.5 g each of spiceries, i.e., Tarragon, Dill Seed, Parsley, Turmeric, and Nutmeg, were separately added to 5 ml of dichloromethane, each mixture was ground in a mortar with a pestle to extract ingredients, and the whole was centrifuged to obtain a supernatant, which was then evaporated to obtain an extract. Each extract obtained from the above-mentioned spiceries was dissolved in 4 ml of ethanol to prepare a solution.

On the other hand, aqueous solutions of 4 mg/ml of uracil, cytocine, adenine, guanine and hypoxanthine were prepared.

10 ml each of a medium containing 4% glucose and 1% yeast extract (pH 6.0) was put into test tubes, and autoclaved, and to the test tubes were added 50 μl of the above-prepared solutions, and 100 μl each of a spore suspension of *Mortierella Alpina* IFO 8568 was inoculated to the media. Culturing was carried out for six days at 28° C. with shaking at 300 rpm, cells were obtained from each cultured broth, and the cells were treated by the same procedures as described in Example 1, to determine the amount of bishomo-γ-linolenic acid obtained from each culture. The results are shown in Table 5.

TABLE 5

| Amount of bishomo-γ-linolenic acid produced (g/l broth) | |
| --- | --- |
| Additive | Amount of product |
| Tarragon extract | 0.55 |
| Dill Seed extract | 0.43 |
| Parsley extract | 0.37 |
| Turmeric extract | 0.75 |
| Nutmeg extract | 0.45 |
| Uracil | 0.25 |
| Cytocine | 0.22 |
| Adenine | 0.35 |
| Guanine | 0.27 |
| Hypoxanthine | 0.25 |

As a comparison, an amount of bisphomo-γ-linolenic acid produced from a culture without an additive was 0.18 g/l.

EXAMPLE 13

The same procedure as described in Example 12 was repeated except that the Turmeric extract was used as an additive and various producer strain were cultured. The results are shown in Table 6.

TABLE 6

| | Amount of bishomo-γ-linolenic acid per medium produced (mg/l) | |
| --- | --- | --- |
| | Turmeric extract | |
| Producer strain | Absent | Present |
| Conidiobolus heterosporus CBS 138.57 | 40.3 | 250.3 |
| Pythium irregulare CBS 494.86 | 9.7 | 25.4 |
| Phytophthora infestans IFO 4872 | 10.8 | 32.7 |
| Penicillium cyaneum IFO 5337 | 7.6 | 15.4 |
| Cladosporium claudosporiodes IFO 30314 | 2.3 | 8.8 |
| Mucor ambigus IFO 6742 | 3.5 | 12.9 |
| Aspergillus candidas IFO 8816 | 8.9 | 20.5 |
| Phodotorula glutinis IFO 0695 | 3.4 | 6.5 |
| Fusarium oxysporum IFO 5942 | 4.0 | 7.7 |

As seen from Table 6, the Turmeric extract enhanced the production of bishomo-γ-linolenic acid for all strains tested.

EXAMPLE 14

As lignan compounds other than those described above, sesamolin (compound A) from a crude sesame oil; and 2-(3,4-methylenedioxyphenyl)-6-(3-methoxy-4-hydxoxyphenyl)-3,7-dioxabicyclo [3.3.0] octane (compound B), 2.6-bis-(3-methoxy-4-hydroxyphenyl)-3,7-dioxabicyclo [3.3.0] octane (compound C), and 2-(3,4-methylene dioxyphenyl)-6-(3-methoxy-4-hydroxyphenoxy)-3,7-dioxabicyclo [3.3.0] octane (compound D) from sesame seeds were known. Using the same procedures as described in Examples 8 and 11, the above-mentioned compounds were isolated and recovered by high performance liquid chromatography.

2 ml each of a medium containing 4% glucose, 1% yeast extract, and 0.01% the compound A, B, C or D was put into 10 ml Erlenmeyer flask and autoclaved at 120° C. for 20 minutes, 100 μl of a spore suspension of Mortierella alpina IFO 8568 was inoculated to the media, and culturing was carried out on a reciprocating shaker at 110 rpm, for eight days at 28° C. After culturing, the filtration of the cultured broth, washing of the cells with water, drying the cells, hydrolysis of the fatty acids, methyl-esterification of the fatty acids, and extraction of the methyl esters were carried out by the same procedures as described in Example 1, to obtain a mixture of the fatty acid methyl esters, The mixture was analyzed by gas chromatography, and the results are shown in Table 7.

TABLE 7

| Amount of bishomo-γ-linolenic acid per medium produced (mg/l) | |
| --- | --- |
| Additive | Amount of product |
| Compound A | 0.74 |
| Compound B | 0.63 |
| Compound C | 0.59 |
| Compound D | 0.66 |

As seen from Table 7 by adding the compound A, B, C, or D, a large amount of bishomo-γ-linolenic acid was produced.

It is clear from the above-mentioned results, that haedoxane-related compounds having a basal structure similar to the above-mentioned compound are effective as additives for the present invention.

We claim:

1. A process for a production of bishomo-γ-linolenic acid, comprising the steps of:

culturing a microorganism capable of producing arachidonic acid in a culture medium containing an additive selected from the group consisting of sesame oil, peanut oil and a mixture thereof to produce bishomo-γ-linolenic acid or a lipid containing bishomo-γ-linolenic acid; or adding the additive to a culture medium in which the microorganism has been grown, and then further culturing the microorganism to produce bishomo-γ-linolenic acid or a lipid containing bishomo-γ-linolenic acid; and recovering the bishomo-γ-linolenic acid.

2. A process for a production of a lipid containing bishomo-γ-linolenic acid, comprising the steps of:

culturing a microorganism capable of producing arachidonic acid in a culture medium containing an additive selected from the group consisting of sesame oil, peanut oil and a mixture thereof to produce a lipid containing bishomo-γ-linolenic acid; or adding the additive to a culture medium in which the microorganism has been grown, and then further culturing the microorganism to produce a lipid containing bishomo-γ-linolenic acid; and recovering the lipid containing bishomo-γ-linolenic acid.

3. A process for a production of bishomo-γ-linolenic acid, comprising the steps of:

culturing a microorganism capable of producing arachidonic acid in a culture medium containing an additive selected from the group consisting of an extract from sesame oil with a solvent which is substantially immiscible with the sesame oil and an extract from sesame seeds with a solvent which is substantially immiscible with the sesame oil to produce bishomo-γ-linolenic acid or a lipid containing bishomo-γ-linolenic acid; or adding the additive to a culture medium in which the microorganism has been grown, and then further culturing the microorganism to produce bishomo-γ-linolenic acid or a lipid containing bishomo-γ-linolenic acid; and recovering the bishomo-γ-linolenic acid.

4. A process for a production of a lipid containing bishomo-γ-linolenic acid, comprising the steps of:
   culturing a microorganism capable of producing arachidonic acid in a culture medium containing an additive selected from the group consisting of an extract from sesame oil with a solvent which is immiscible with the sesame oil and an extract from sesame seeds with a solvent which is immiscible with the sesame oil to produce a lipid containing bishomo-γ-linolenic acid; or adding the additive to a culture medium in which the microorganism has been grown, and then further culturing the microorganism to produce a lipid containing bishomo-γ-linolenic acid; and
   recovering the lipid containing bishomo-γ-linolenic acid.

5. A process for a production of bishomo-γ-linolenic acid, comprising the steps of:
   culturing a microorganism capable of producing arachidonic acid in a culture medium containing an additive selected from the group consisting of sesamin, sesaminol, episesamin, episesaminol, sesamolin, 2-(3,4-methylenedioxyphenyl)-6-(3-methoxy-4-hydroxyphenyl)-3,7-dioxabicyclo [3.3.0]octane, 2,6-bis-(3-methoxy-4-hydroxyphenyl)-3,7-dioxabicyclo [3.3.0]octane, 2-(3,4-methylenedioxyphenyl)-6-(3-methoxy-4-hydroxyphenoxy)-3,7-dioxabicyclo [3.3.0]octane, and a mixture thereof to produce bishomo-γ-linolenic acid or a lipid containing bishomo-γ-linolenic acid; or adding the additive to a culture medium in which the microorganism has been grown, and then further culturing the microorganism to produce bishomo-γ-linolenic acid or a lipid containing bishomo-γ-linolenic acid; and
   recovering the bishomo-γ-linolenic acid.

6. A process for a production of a lipid containing bishomo-γ-linolenic acid, comprising the steps of:
   culturing a microorganism capable of producing arachidonic acid in a culture medium containing an additive selected from the group consisting of sesamin, sesaminol, episesamin, episesaminol, sesamolin, 2-(3,4-methylenedioxyphenyl)-6-(3-methoxy-4-hydroxyphenyl)-3,7-dioxabicyclo [3.3.0] octane, 2,6-bis-(3-methoxy-4-hydroxyphenyl)-3,7-dioxabicyclo [3.3.0] octane, 2-(3,4-methylenedioxyphenyl)-6-(3-methoxy-4-hydroxyphenoxy)-3,7-dioxabicyclo [3.3.0] octane, and a mixture thereof to produce a lipid containing bishomo-γ-linolenic acid; or adding the additive to a culture medium in which the microorganism has been grown, and then culturing the microorganism to produce a lipid containing bishomo-γ-linolenic acid; and
   recovering the lipid containing bishomo-γ-linolenic acid.

7. A process a for production of bishomo-γ-linolenic acid, comprising the steps of:
   culturing a microorganism capable of producing arachidonic acid in a culture medium containing an additive selected from the group consisting of Tarragon extract, Dill Seed extract, Parsley extract, Turmeric extract, Nutmeg extract and a mixture thereof to produce bishomo-γ-linolenic acid or a lipid containing bishomo-γ-linolenic acid; or adding the additive to a culture medium in which the microorganism has been grown, and then further culturing the microorganism to produce bishomo-γ-linolenic acid or a lipid containing bishomo-γ-linolenic acid; and
   recovering the bishomo-γ-linolenic acid.

8. A process for a production of a lipid containing bishomo-γ-linolenic acid, comprising the steps of:
   culturing a microorganism capable of producing arachidonic acid in a culture medium containing an additive selected from the group consisting of Tarragon extract, Dill Seed extract, Parsley extract, Turmeric extract, Nutmeg extract and a mixture thereof to produce a lipid containing bishomo-γ-linolenic acid; or adding the additive to a culture medium in which the microorganism has been grown, and then further culturing the microorganism to produce a lipid containing bishomo-γ-lenolenic acid; and
   recovering the lipid containing bishomo-γ-linolenic acid 9. A process according to claim 1, wherein the microorganism capable of producing arachidonic acid is selected from microorganisms belong to the genera *Mortierella, Conidiobolus, Pythium, Phytophthora, Penicillium, Clasdosporium, Mucor, Fusarium, Aspergillus, Rhodotorula* and *Entomophthora*.

10. A process according to claim 1, wherein the microorganism capable of producing arachidonic acid is selected from the group consisting of *Mortierella elongata* IFO 8570, *Mortierella exiqua* IFO 8571, *Mortierella hygrophila* IFO 5941, *Mortierella alpina* IFO 8568, *Mortierella elongata* SAM 0219, *Mortierella parvispora* IFO 8574, *Conidiobolus heterosporus* CBS 138.57, *Pythium irregulare* CBS 494.86, *Phytophthora infestans* IFO 4872, *Conidiobolus thromoboides* CBS 183.60, *Penicillium cyaneum* IFO 5337, *Cladosporium herbarum* IFO 30314, *Mucor ambiguus* IFO 6742, *Aspergillus candidus* IFO 8816, *Rhodoturula glutinis* IFO 0695, *Fusarium oxysporum* IFO 5942, *Cladosporium sphaerospermum* IFO 6377, and *Entomophthora ignobilis* CBS 181.60.

* * * * *